US008449545B2

(12) United States Patent
Sidebotham et al.

(10) Patent No.: US 8,449,545 B2
(45) Date of Patent: May 28, 2013

(54) LOW COST MODULAR TAPERED HOLLOW REAMER FOR MEDICAL APPLICATIONS

(76) Inventors: Christopher G. Sidebotham, Mendham, NJ (US); Randall J. Lewis, Bethesda, MD (US)

( * ) Notice: Subject to any disclaimer, the term of this patent is extended or adjusted under 35 U.S.C. 154(b) by 788 days.

(21) Appl. No.: 12/072,522

(22) Filed: Feb. 27, 2008

(65) Prior Publication Data

US 2008/0195105 A1 Aug. 14, 2008

Related U.S. Application Data

(63) Continuation-in-part of application No. 11/973,260, filed on Oct. 5, 2007, which is a continuation-in-part of application No. 11/704,754, filed on Feb. 9, 2007.

(51) Int. Cl.
*A61B 17/00* (2006.01)

(52) U.S. Cl.
USPC .............................................. 606/80; 606/79

(58) Field of Classification Search
USPC 606/79–85, 86 R, 87–90, 99, 100; 623/22.12
See application file for complete search history.

(56) References Cited

U.S. PATENT DOCUMENTS

| | | | | |
|---|---|---|---|---|
| 4,116,200 A | 9/1978 | Braun et al. | | 605/81 |
| 4,811,632 A | 3/1989 | Salyer | | 76/115 |
| 5,100,267 A | 3/1992 | Salyer | | 407/54 |
| 5,116,165 A | 5/1992 | Salyer | | 407/54 |
| 5,171,312 A | 12/1992 | Salyer | | 606/81 |
| 5,171,313 A | 12/1992 | Salyer | | 606/86 |
| 5,190,548 A | 3/1993 | Davis | | 606/80 |
| 5,229,893 A * | 7/1993 | Dworatzek et al. | | 386/47 |
| 5,236,433 A | 8/1993 | Salyer | | 606/91 |
| 5,282,804 A | 2/1994 | Salyer | | 606/86 |

(Continued)

FOREIGN PATENT DOCUMENTS

| | | | |
|---|---|---|---|
| EP | 0 296 986 | * | 6/1988 |
| WO | WO/9007908 | | 7/1990 |

OTHER PUBLICATIONS

"Effect of Flexible Drive Diameter and Reamer Design on the Increase of Pressure in the Medullary Cavity During reaming", Mueller et al., PubMed (1993) http://www.ncbi.nlm.nih.gov/entrez/query.fcgi?db=pubmed&cmd=Retrieve&dopt=AbstractPlus&list_uids=8168875&query_hl=2&itool=pubmed_Brief.

(Continued)

*Primary Examiner* — Matthew Lawson
(74) *Attorney, Agent, or Firm* — Ernest D. Buff; Ernest D. Buff & Assoc. LLC; Margaret A. LaCroix, Esq.

(57) ABSTRACT

An easy-to-assemble modular reamer for medical applications includes a shaft portion, a disposable tapered hollow reamer and a modular pilot. The shaft portion has a proximal end for attachment to a drill, two or more torque transmitting tabs and a distal threaded end. The disposable tapered hollow reamer has an integrally attached cutter sleeve with externally protruding cutters, apertures through the sleeve thickness for discharging bone fragments and cement debris and inwardly protruding anchoring projections. A central molded polymeric portion attaches to the anchoring projection and is fixed to the shaft through central holes and slots in the polymeric portion, which engage torque transmitting shaft tabs. Channels in the polymeric portion collect bone fragments and bone debris. A threaded modular pilot coaxially secures the disposable tapered hollow reamer to the threaded distal end of the shaft, permitting rotation of the tapered hollow reamer without wobbliness.

14 Claims, 5 Drawing Sheets

U.S. PATENT DOCUMENTS

| | | | | |
|---|---|---|---|---|
| 5,295,992 | A * | 3/1994 | Cameron | 606/79 |
| 5,299,893 | A | 4/1994 | Salyer | 407/54 |
| 5,376,092 | A | 12/1994 | Hein et al. | 606/81 |
| 5,501,686 | A | 3/1996 | Salyer | 696/79 |
| 5,549,613 | A | 8/1996 | Goble et al. | 606/80 |
| 5,556,399 | A | 9/1996 | Huebner | 606/80 |
| 5,690,634 | A | 11/1997 | Muller et al. | 606/80 |
| 5,709,688 | A | 1/1998 | Salyer | 606/81 |
| 5,755,719 | A | 5/1998 | Frieze | 606/81 |
| 5,817,096 | A | 10/1998 | Salyer | 606/81 |
| 5,954,671 | A | 9/1999 | O'Neill | 600/567 |
| 5,976,144 | A | 11/1999 | Fishbein et al. | 606/80 |
| 5,976,148 | A * | 11/1999 | Charpenet et al. | 606/91 |
| 5,980,170 | A | 11/1999 | Salyer | 408/239 R |
| 6,001,105 | A | 12/1999 | Salyer | 606/81 |
| 6,053,922 | A * | 4/2000 | Krause et al. | 606/80 |
| 6,120,508 | A * | 9/2000 | Grunig et al. | 606/85 |
| 6,168,599 | B1 * | 1/2001 | Frieze et al. | 606/80 |
| 6,168,600 | B1 | 1/2001 | Grace et al. | 606/81 |
| 6,193,722 | B1 | 2/2001 | Zech et al. | 606/79 |
| 6,261,295 | B1 * | 7/2001 | Nicholson et al. | 606/87 |
| 6,283,971 | B1 * | 9/2001 | Temeles | 606/81 |
| 6,332,886 | B1 * | 12/2001 | Green et al. | 606/80 |
| 6,409,732 | B1 | 6/2002 | Salyer | 606/91 |
| 6,428,543 | B1 | 8/2002 | Salyer | 606/81 |
| 6,447,518 | B1 * | 9/2002 | Krause et al. | 606/80 |
| 6,451,023 | B1 | 9/2002 | Salazar et al. | 606/86 |
| 6,730,094 | B2 | 5/2004 | Salyer et al. | 606/80 |
| 6,875,217 | B2 | 4/2005 | Wolford | 606/81 |
| 7,074,224 | B2 * | 7/2006 | Daniels et al. | 606/80 |
| 7,229,078 | B2 * | 6/2007 | Lechot | 279/93 |
| 7,278,996 | B2 * | 10/2007 | Wolford | 606/81 |
| 2003/0181916 | A1 | 9/2003 | Wolfdord | 606/81 |
| 2004/0267266 | A1 * | 12/2004 | Daniels et al. | 606/80 |
| 2005/0113836 | A1 | 5/2005 | Lozier et al. | 606/80 |
| 2006/0004371 | A1 * | 1/2006 | Williams et al. | 606/80 |
| 2006/0095041 | A1 | 5/2006 | Fehlbaum et al. | 606/81 |
| 2006/0106393 | A1 * | 5/2006 | Huebner et al. | 606/80 |
| 2006/0184174 | A1 | 8/2006 | Harris et al. | 606/80 |
| 2006/0229625 | A1 * | 10/2006 | Truckai et al. | 606/79 |
| 2006/0235539 | A1 | 10/2006 | Blunn et al. | 623/22.12 |
| 2006/0264956 | A1 | 11/2006 | Orbay et al. | 606/80 |
| 2007/0088361 | A1 * | 4/2007 | Ho | 606/80 |
| 2007/0162033 | A1 * | 7/2007 | Daniels et al. | 606/80 |
| 2007/0233127 | A1 * | 10/2007 | Tuke et al. | 606/79 |
| 2007/0233131 | A1 * | 10/2007 | Song et al. | 606/79 |
| 2007/0233132 | A1 * | 10/2007 | Valla | 606/81 |

OTHER PUBLICATIONS

"Single Use Sterile Power Equipment", Orthomedix.com, at http://www.orthomedex.com/index.html.

* cited by examiner

Prior Art

Fig 3.
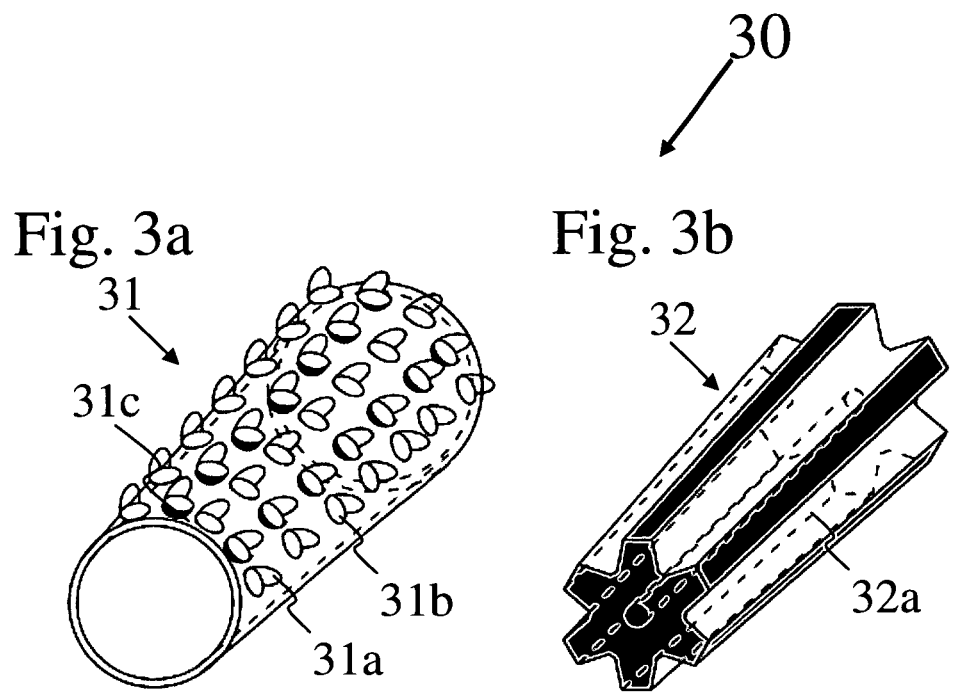
Fig. 3a
Fig. 3b
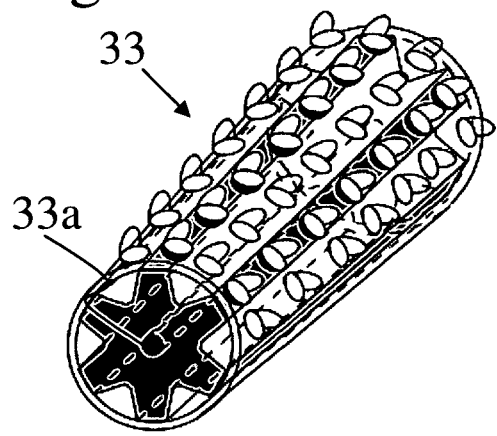
Fig. 3c

LOW COST MODULAR TAPERED HOLLOW REAMER FOR MEDICAL APPLICATIONS

This is a Continuation-In-Part of application Ser. No. 11/973,260, filed Oct. 5, 2007 for "Modular Tapered Hollow Reamer For Medical Applications" which, in turn, is a Continuation-In-Part of U.S. Ser. No. 11/704,754, Filed Feb. 9, 2007 for "Hollow Reamer For Medical Applications", the disclosures of which are hereby incorporated in their entirety by reference thereto.

BACKGROUND OF THE INVENTION

1. Field of the Invention

The present invention relates to a modular, easy-to-assemble, tapered, hollow reamer for medical applications; and more particularly, to a modular, tapered, hollow reamer that is inexpensive to produce and has a disposable reamer assembly, which can be attached to a reusable shaft portion and includes one or more bone debris capturing cavities.

2. Description of the Prior Art

Reaming of the internal canal of bones is required in many surgical procedures of orthopedic surgery. These procedures include hip replacement, knee replacement and shoulder replacement. Reamers are also used in procedures that involve the internal fixation of fractures. Prior art reamers typically fall into two major classes: rigid and flexible shaft. Typically, reaming of the internal bone canal is achieved through utilization of a solid cylindrical or tapered reamer. Solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer acquires dull cutting edges, its bone cutting efficiency is substantially reduced. In such cases the reamer can generate sufficient friction/heat to damage or kill the surrounding bone. These prior art solid cylindrical or tapered reamers are intended for multiple uses and therefore become less efficient after each surgery, resulting in poor cutting performance and bone necrosis. Dull reamer blades can also incorporate bone debris or bone cement debris into the living bone tissue, creating bone healing problems.

U.S. Pat. No. 4,116,200 to Braun et al. discloses a milling tool for surgical purposes. The surgical milling tool is a hand-operated milling machine for milling the heads or sockets of bone joints and has a spherical shape. The tool is formed of a hemispherical cup integrally formed with a cylindrical skirt and flange and is provided with a plurality of openings of semi-oval shape, each having a cutting edge arranged at the minor axis of the oval shape. The openings are situated such that, upon rotation of the cup, the cutting edges thereof overlap to provide a continuous cutting edge surface conforming generally to the shape of the cup. The hemispherical shape of the cup provides the ability to hollow out the arcuate shape of the bone joints. Bone and cartilage shavings are formed during the milling process and are collected in a border area inside of the hemispherical cup. The surgical milling tool is provided for multiple uses and therefore the tool will become less efficient after each surgery, resulting in poor cutting performance and bone necrosis. Moreover, the spherically shaped reaming tool is not tapered.

U.S. Pat. No. 5,190,548 to Davis discloses surgical reamer. This surgical bone reamer includes a rotatable, elongated shank having a proximal end, a distal end and a longitudinal axis. A reaming head mounted on the distal end. A plurality of equally spaced walls is radially disposed on the reaming head around the longitudinal axis. Tip edges for penetrating bone are defined on the radial walls to be disposed angularly with the longitudinal axis. Reaming edges joined to the tip edges extend longitudinally from the tip edges in the proximal direction parallel to and an equal radial distance from the longitudinal axis for reaming a cylindrical tunnel when the reaming head is rotated in bone. Tapered flutes disposed angularly between the tip edges and the radial walls permit bone to be evacuated through the reaming head when forming a tunnel in bone. The reaming head is provided with angular tips and edges for penetrating the bone and is thus not a single use disposable cutter. The debris created is not stored away from the cutting edge and thus previously cut material may be included in the bone.

U.S. Pat. No. 5,549,613 to Goble et al. discloses a modular surgical drill. This modular surgical drill is in the form of a rigid drill shaft and a drill bit, which are connected together by a tongue-and-groove arrangement attaching the rear end of the drill bit to the forward end of the drill shaft. Each of the shaft and drill bit are provided with through bores extending centrally through their entire length. These bores become aligned upon assembly of the drill bit and shaft. The modular drill is intended to be employed with a guidewire for drilling holes into bone. The assembled drill bit and shaft are placed on the guidewire and moved down such guidewire into contact with the bone, whereupon a tunnel may be formed into the bone by rotating and advancing the drill bit along the guidewire. The dimensions of the bore and guidewire are so selected as to prevent the drill bit and drill shaft from moving relative to one another once they are assembled and mounted on the guidewire. Debris created during drilling is not removed and collected away from the cutting location. The central bore is solid and as such does not receive cut bone debris. The cutter used is not disposable.

U.S. Pat. No. 5,556,399 to Huebner discloses a bone-harvesting drill apparatus and method for its use. A coring drill harvests bone from a donor area of the human body. The drill bit is formed with a cylindrical, hollow shaft and a half-conical tip or cutting head. The cutting head is provided with a sharpened edge, which meets at an apex with a non-sharpened edge, forming an obtuse angle of approximately 120 degrees. The sharpened edge is configured to cut into bone when the drill bit is rotated in a clockwise direction. With the apex directed against a section of bone, the cutting edge sheers off fragments of bone, which are then drawn upwardly through the hollow shank of the drill bit. As the drill bit is forced downwardly, continuous cutting action occurs and the morselized bone can then be removed from the shank and used to build-up bone in other areas to which it is transplanted. The drill bit fittingly mates on the distal end a fitting that renders the drill bit physically compatible with a conventional chuck. The bit includes a pair of diametrically opposed, oppositely inclined recesses that cooperate with a crossbar member within a bit-receiving bore of the fitting. When the aligned drill bit is pressed into the fitting, the crossbar member cams along the inclined recesses causing the bit to rotate relative to the fitting. The resulting frictional engagement between the recesses and the crossbar member, along with a detent assembly between the bit and the fitting, securely lock the bit onto the distal end of the fitting, yet render removal possible by the use of a removal tool. The bone harvesting tool provides a non-disposable cutter. Reuse of the cutter dulls the beveled lip edges. Moreover, the harvested bone collection central bore requires a thorough cleaning prior to each use, creating contamination possibilities.

U.S. Pat. No. 5,690,634 to Muller et al. discloses a medullary drill head. This drill head for intramedullary drilling has a front part, a middle part and a rear part and is shaped as a hollow body of revolution. The front and rear parts have spiral slots formed with cutting edges. The rear part has an attachment for coupling to a drilling shaft. The drill head is not disposable, and as a result, the drill head is continuously reused, resulting in dulling of the cutting edges. Moreover, the drill head includes three openings in the form of spirally shaped slots configured to have cutting edges similar to a grater; and has no place to collect bone debris.

U.S. Pat. No. 5,954,671 to O'Neill discloses a bone harvesting method and apparatus. This apparatus and method harvests bone using a manual, cylindrical, multi-directional coring device with a guided delivery system that can be inserted through a percutaneous or closed approach to extract precisely measured amounts of bone or bone marrow. A series of guide wires, obturators, dilators and cannulas are used as the exposure and delivery instrumentation for a cutting tool. The cutting tool has a tip with six cutting edges for cutting in all directions. This apparatus is a manual, cylindrical, multi-directional coring device with a guided delivery system to extract precisely measured amounts of bone or bone marrow. The cutter portion of the device is not disposable and is subject to wear and dull edges. This coring device does not suggest a tapered reamer.

U.S. Pat. No. 5,976,144 to Fishbein et al. discloses a hollow dome reamer with removable teeth. This surgical reamer has a hollow dome with apertures spaced apart arranged in arcs extending from an apex of the dome to the base portion of the dome, and removable teeth positioned in the apertures. Each cutting tooth has (i) a flange that is aligned flush with the external surface of the dome, (ii) a raised cutting edge extending above the flange and the external surface of the dome, and (iii) an interior passageway communicating between the outside and inside of the dome. A base plate may be removably secured on the base portion of the dome to provide closure for the central cavity of the dome. Although the teeth are removable, they are not disposable in nature; the teeth are removed for replacement or for re-sharpening and are used again. Removal of the small teeth may be cumbersome and difficult, and may even pose a danger during removal as the person removing the teeth may be cut by the sharp edges; replacement of the teeth into the apertures of the reamer will likely pose the same problems. The bone debris is not collected away from the cutting edges of the teeth. This hollow domed reamer is spherically shaped reamer; does not suggest a tapered reamer.

U.S. Pat. No. 5,980,170 to Salyer discloses a tool driver. This tool driver has a shaft with a longitudinal axis and opposite ends. A boss is secured at one of the shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool, which is used with the driver has a bar containing the same dimensions as the groove in the boss of the tool driver. The bar thus fills and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned. The cutters are connected to the tip of the shaft and are spherical in nature for joint and patella reaming. In addition, the reamer cups are not disposable in nature. The bone fragments are not collected and kept away from the cutting edge. This spherically shaped reamer is not tapered.

U.S. Pat. No. 6,193,722 to Zech et al. discloses a hollow milling tool. The hollow milling tool produces substantially hollow cylindrical depressions in human or animal tissue. It also produces tissue pillars, which are removed at a harvest location, transported to a defect location and implanted. The hollow milling tool has teeth for the ablation of tissue which are arranged at the distal end of the milling tool at the end side. Furthermore, the milling tool has passages for transporting a cooling fluid to a cooling region of the milling tool lying near the distal end during the ablation of tissue. Teeth are constructed within the milling tool for accomplishing the depressions. These teeth will eventually need sharpening as the tool is used over time. No structure is contained within the '722 patent that discloses or suggests a tapered reamer.

U.S. Pat. No. 6,332,886 to Green et al. discloses a surgical reamer and method of using same. This device is used for expedited reaming of a medullary canal. The device includes a reamer head connected at the distal end of a rotatable drive shaft. The reamer head has a cutting head with five blades and flutes therebetween. Each blade has a front cutting portion. The blades can also include a side cutting portion. The method for removing material from the medullary canal of a bone includes the steps of reaming an area of the medullary canal to remove material; irrigating the material to be removed while reaming to reduce generation of heat and move removed material from the reaming area; and aspirating the removed material while reaming to create a negative intramedullary canal pressure to assist in the removal of the material. The blades and flutes at the reamer are reused and are subject to dulling. The bone chips are to be removed by the irrigating fluid, which means they are always present adjacent to the cutting portions and may be forced into the bone tissue. No disclosure in the '886 patent suggests a tapered reamer.

U.S. Pat. No. 6,451,023 to Salazar et al. discloses a guide bushing for a coring reamer, a storage package for reamer assembly, and a method of use. This guide bushing for a coring reamer has a tapered member with its largest diameter at its first end so that the guide bushing frictionally engages an internal surface of the reamer with a line contact. The guide bushing has a passage sized to slidably receive a guide pin. In use, the bushing advances in the proximal direction within the coring reamer along a guide pin while the excavated bone enters the passageway through the reamer. A storage package specifically designed for the reamer assembly is employed to remove the excavated bone from within the reamer. The package has a closed distal end and an open proximal end closeable with a cap. With the coring reamer received in cantilevered fashion through a central opening of the cap of the tube, and with an adapter that couples the coring reamer to a handpiece installed, a wrench is placed over the adapter and turned while the user grips peripheral surfaces of the cap to prevent rotation of the coring reamer. A plunger is inserted through the opening and through the coring reamer from the proximal end. The plunger is pushed through the reamer until the bone core and bushing fall out of the distal end of the coring reamer. The guide bushing for a coring reamer is appointed with an open end surrounded by peripheral teeth. The teeth are arranged peripheral to the body of the tube of the reamer. The tube is hollow and therefore excavated bone accumulates therewithin. The reamer, bushing and packaging are disposed of after use. The '023 patent discloses a bone excavating tool that does not prepare a bone canal for implantation of femoral implants. No structure is disclosed therein that suggests a tapered reamer.

U.S. Pat. No. 7,074,224 to Daniels et al. discloses a modular tapered reamer for bone preparation and associated method. This kit is for use in performing joint arthroplasty and includes a trial and a reamer. The reamer is said to be useful when preparing a cavity in the intramedullary canal of a long bone with the use of a driver, and to assist in performing a trial reduction. The reamer includes a first portion for placement at least partially in the cavity of the long bone and a second portion operably connected to the first portion. The reamer is removably connected to the driver to rotate the reamer. The trial is removably attachable to the reamer. This tapered reamer is not disposable and does not have provision for accumulating bone debris away from the cutting portion of the bone.

U.S. Patent Application Publication No. 2005/0113836 to Lozier et al. discloses an expandable reamer. This expandable reamer includes a cannulated shaft and a plurality of straight cutting blades having deformable points. The blades are hingably outwardly rotatable at the deformation points between a contracted position and an expanded position. In the contracted position, the blades are substantially parallel to the longitudinal axis of the cannulated shaft and, in the expanded position, the blades have at least a portion oriented radially outward from the longitudinal axis, thereby forming a larger diameter cutting surface in the expanded position and in the contracted position. The blades are formed from a portion of the cannulated shaft by, e.g. milling longitudinally extending slots through the wall of the cannulated shaft. The slots serve as flutes dividing the cutting edge and trailing edge of each adjacent blade. Each blade may also include more than one segment arranged along its length, the segments being coupled by deformation points. The expandable reamer may be used for cutting a cavity in a bone or other structure that is larger than the diameter of the entry point into the bone and greater than the diameter of the contracted reamer. The expandable reamer is not disposable. Since the expandable blades are deformably attached to the cannulated shaft, the cut bone debris is not collected away from the bone cutting region. As a result, fragments of cut bone debris may be pushed into the bone tissue by the deformable rotating blades.

U.S. Patent Application Publication No. 2006/0004371 to Williams et al. discloses an orthopedic reamer. This orthopedic reamer is for use in creating and sizing canals in a bone. The orthopedic reamer includes a non-polymeric cutting portion having at least one cutting surface thereon and a polymeric body portion covering at least a portion of the cutting portion. The at least one cutting surface is not covered by the polymeric body portion. The orthopedic reamer provides cutting components including a blade or saw like construction, rather than the plurality of teeth. Although the orthopedic reamer is appointed for disposability, the publication requires that the entire reamer, and not just the cutting portion, be disposed of. That is to say, the entire reamer, including the non-polymeric cutting portion and the polymeric body portion of the device are all disposed of; not just the cutter.

There remains a need in the art for a low cost, modular, easy-to-assemble, hollow tapered reamer for medical applications having a disposable hollow cutter assembly. Also needed in the art is a disposable hollow cutter assembly of the type described, which can be attached to a reusable shaft portion that provides means for reaming of the internal canal of bones. Further needed in the art is a cutter assembly having means for collecting bone debris and keeping the collected debris displaced from the cutting edges, so that the cutting edges remain during drilling and after one use of the reamer a new hollow cutter assembly can be utilized, and the old hollow cutter assembly can be discarded.

SUMMARY OF THE INVENTION

The present invention provides a low cost, modular, easy-to-assemble hollow tapered reamer for medical applications having a disposable cutter assembly. The cutter assembly is attached to a reusable shaft portion of the reamer and has a space for bone debris collection, which prevents inclusion of bone and bone cement debris into the living bone tissue. The reusable shaft portion has a central shaft with torque transmitting tabs that engage with corresponding slots in the polymeric portion of the low cost modular disposable hollow tapered reamer. The reusable shaft is threaded at the distal end to secure the low cost modular tapered hollow disposable cutter. A threaded modular pilot is provided securing the low cost modular tapered hollow disposable cutter to the shaft. The threading is of an orientation that the connection between the shaft and the low cost modular tapered hollow disposable cutter does not loosen as the shaft is rotated during the reaming operation. Preferably, a fresh tapered hollow reamer is used with each new application. The tapered hollow reamer includes a plurality of apertures and is hollow to allow space between the reamer and the reusable shaft for bone and bone cement debris collection. It is attached to a shaft using a modular pilot with a threaded connection. Torque from the shaft is transferred to the reamer through the tabs that transfer the torque to the polymeric member which integrally connected to cutting blades, providing bone cutting action. Thus when a drill or other hand machinery rotates the reusable shaft, the shaft torque is transferred to the reamer through the tabs while the reamer is held securely at the centerline of the rotating reusable shift, preventing any wobbly motion. This disposable sharp hollow reamer therefore reduces heat generated during cutting by removing the bone debris from the outer surface of the reamer to the inside of the reamer, while the bone debris collected may be used later for bone grafting and other specific surgical procedures. A further advantage of the hollow design is that by allowing the removal of the bone debris from the outer surface of the reamer to the inside of the cutter, the reamer is less likely to raise the intramedulary pressure in the long bone being reamed, thereby lessening the chance of fat embolism during these procedures. Also fragments of bone chips or bone cement are not incorporated in the living bone tissue by the reamer cutting action.

Generally stated, the reamer for medical applications comprises: (a) a reamer reusable shaft having an elongated body with a proximal end, one or more torque transmission tabs in the central portion, said proximal end having a coupling portion appointed for attachment of said reamer to a drilling device, said distal end having a threaded portion; (b) said torque transmission tabs of said reamer reusable shaft engaging with a tapered poured or injection molded polymeric portion of a low cost disposable hollow reamer assembly; (c) a disposable tapered hollow reamer assembly comprising: (1) in a first embodiment a tapered metallic sleeve with a plurality of cutter elements protruding from the outer surface of the sleeve, a plurality of apertures adjacent to the cutters, a plurality of anchoring protrusions extending into the interior of the sleeve for engaging with a poured or injection molded polymeric portion; (2) in a second embodiment a polymeric sleeve with a plurality of apertures, some apertures discharging bone debris and some apertures being designed to receive along a line plurality of metallic cutter elements that has both cutting protrusions extending outward from the polymeric sleeve and anchoring protrusions extending inwards into the interior of the sleeve; (3) the metallic or polymeric sleeve permanently bonded to a poured or injection molded polymeric portion anchoring the metallic sleeve or polymeric sleeve with inserted metallic cutting elements along a line where anchoring protrusions are present; (4) said poured or injection molded polymeric portion having bone debris or bone cement gathering chamber directly below the apertures of metallic sleeve or polymeric sleeve; (5) said poured or injection molded polymeric portion having a central aperture with torque transmitting slots for receiving a reusable shaft with one or more torque transmitting tabs (d) a pair of end plates to constrain bone fragments and bone cement debris collected; and (e) a modular pilot that engages said poured or injection molded polymeric portion with integrally attached cutters with the shaft distal end threads of the reusable shaft thereby centering said tapered hollow reamer assembly along the rotational axis of the reusable shaft.

The present invention of modular tapered reamer solves the problems associated with the prior art reamers. In accordance with the present invention, the low cost modular tapered hollow reamer for medical applications has an easy-to-assemble, disposable, modular, hollow tapered reamer with a cutting sleeve and a central polymeric poured or injection molded portion, which can be attached to a reusable shaft using torque transmitting shaft tabs and a modular pilot that allows for a fresh cutter to be used with each new application of the reamer. The low cost modular tapered hollow reamer of the present invention transfers shaft torque reliably while at the same time maintains the centerline of the reamer preventing wobbliness thereof during cutting. Bone and bone cement fragments are collected and stored away from the bone cutting area thereby reducing the possibility of bone fragment incorporation into living bone tissue. The low cost modular tapered hollow reamer gradually crates the bone cavity due to the taper provided, thereby reducing heat during its surgical usage. Owing to the presence of these features, the low cost modular tapered hollow reamer of this invention is safer to use and operates more efficiently than prior art reamers.

BRIEF DESCRIPTION OF DRAWINGS

The invention will be more fully understood and further advantages will become apparent when reference is had to the following detailed description of the preferred embodiments and the accompanying drawings, in which:

FIG. 3 depicts in three views, FIG. 3a, FIG. 3b and FIG. 3c, a perspective view of the mechanical details of construction of the low cost disposable tapered hollow reamer according to the first embodiment of the invention;

FIG. 4c FIG. 4d and FIG. 4e, a perspective view of the mechanical details of construction of the low cost disposable tapered hollow reamer according to the second embodiment of the invention.

DESCRIPTION OF THE PREFERRED EMBODIMENTS

Figure 1:
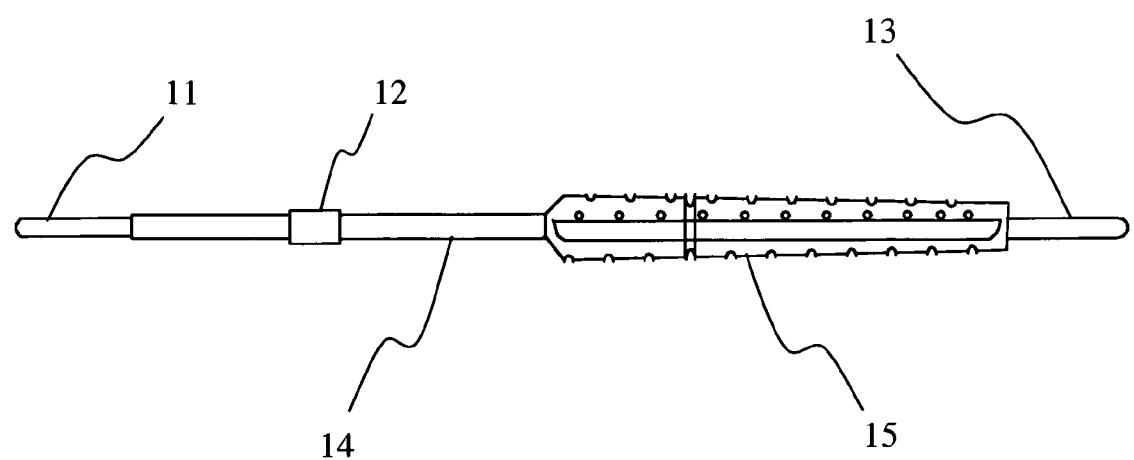
FIG. 1 is a perspective view depicting a medical tapered reamer found in the prior art.

Reaming of the internal canal of bones is required during many orthopedic surgical procedures. These procedures include hip replacement, knee replacement and shoulder replacement. Other surgical procedures that see the use of reamers include internal fixation procedures for fractures. Typically, reaming of the internal bone canal is achieved through utilization of a solid cylindrical or tapered reamer, illustrated in FIG. 1. Prior art reamers typically include a driver coupling 11 (shown as a Jacob chuck connector), a size designation 12, a pilot tip 13, a shaft 14, and cutting flutes 15. FIG. 1 shows a tapered reamer, however cylindrical reamers of similar design also exist in the prior art. Those solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. The bone or bone cement debris collected is pushed against the living bone tissue and may be incorporated into the bone. Currently utilized solid cylindrical or tapered reamers are intended for multiple uses and therefore become less efficient after each surgery, resulting in poor cutting performance and bone necrosis.

Figure 2:
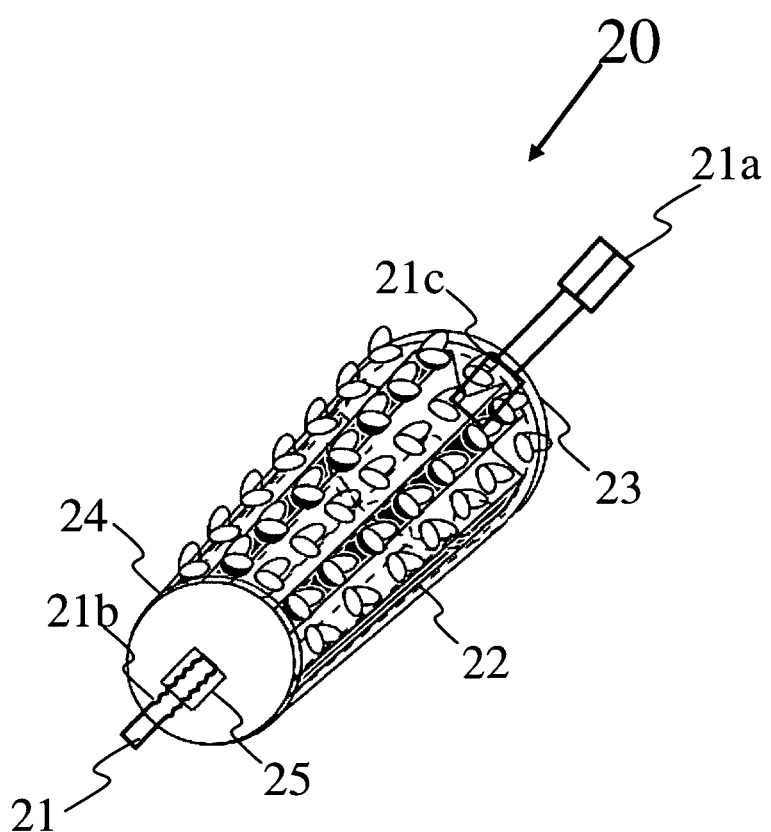
FIG. 2 is a perspective view depicting a medical tapered reamer of the subject invention assembled on a reusable shaft.

FIG. 2 depicts at 20 the low cost modular disposable tapered hollow reamer assembly of the present invention, which provides the low cost disposable hollow reamer 22 attached to a shaft 21 appointed for use in medical applications. Due to its taper, it gradually enlarges the diameter of the bone canal reducing the amount of pressure applied to the bone. A number of sizes of tapered hollow reamers are available along with their shafts and modular pilots so that the surgeon can choose progressively larger hollow tapered reamers for a fresh bone canal or a reworked bone canal. Since the low cost tapered hollow reamer 22 is disposable, the cutting performance of the hollow reamer is not compromised through repeated use. Several limitations of the prior art reamers and consequent clinical problems seen are overcome through utilization of the disposable modular tapered hollow reamers herein. Novel design features of the hollow reamers of the present invention and improvements to prior art reamers are multifaceted. The design includes a low cost disposable hollow tapered reamer 22 with a central poured or injection molded polymeric portion and reusable shaft 21 with two or more lateral tabs 21c engaging with corresponding slots in the poured or injection molded polymeric portion of the low cost disposable tapered hollow reamer. The distal end of the shaft is threaded at 21b with a thread engaging a modular pilot 25. During this attachment, end plates 23 and 24 are inserted to contain bone fragments and bone cement debris. The shaft has a driver coupling 21a (shown as a Jacob chuck connector). The shaft 21 is attached to a drill at 21c. A number of shaft sizes can be selected from a kit and the shaft size is indicated in a shaft marking. The modular pilot 25 may carry indicia representing a shaft size to which it may be connected. Moreover, when dealing with revision hip surgery, the hollow reamers have also been designed to cut bone cement (PMMA) in a more efficient manner by providing internal space within the low cost tapered hollow reamer to capture the debris. This feature reduces both the cutting temperature and time required to remove the remnant cement mantle. The bone debris collected may be used for bone grafting or other specific surgical procedures. A further advantage of the hollow design is that by allowing the removal of the bone debris from the outer surface of the reamer to the inside of the reamer, the reamer is less likely to raise the intramedulary pressure in the long bone being reamed, thereby lessening the chance of fat embolism during these procedures.

FIG. 3 depicts at 30 the mechanical details of the low cost modular disposable tapered hollow reamer according to the first embodiment of the invention in three views FIG. 3a, FIG. 3b and FIG. 3c. FIG. 3a illustrates a metallic cutting sleeve 31 that has cutting protrusions 31a extending from the outer surface. Apertures 31b allow bone fragments and bone cement debris cut to enter the interior hollow portion of the sleeve 31. Several of the cutters in specific locations have protrusions 31c extending into the hollow interior of the metallic sleeve. These protrusions 31c engage with poured or injected polymer 32 of FIG. 3b to permanently anchor the metallic cutting sleeve to the poured or injection molded polymeric portion thereby providing torque transmission between the poured or injected polymer portion and the hollow metallic sleeve 31. As shown at 32 of FIG. 3b, the injection molding of the polymer is prevented from reaching the hollow metallic sleeve in several locations forming channels 32a that provide a space for collecting bone debris. FIG. 3c shows at 33 the low cost disposable tapered hollow reamer in the manufactured state as it is provided to a customer. The figure shows no protrusions of the cutting elements in the channel regions, while optionally, these protrusions may be present in each and every one of the cutting elements. The polymeric sleeve and the poured or injection molded polymer is a medically compatible resin such as an acetyl resin or a polysulfone resin. The polymeric portion has a central aperture 33a drilled to receive a reusable shaft. On the opposite side, (not shown) the polymeric portion has two or more slots machined to engage with the torque transmitting tabs (21c of FIG. 2) of the shaft.

Figure 4:
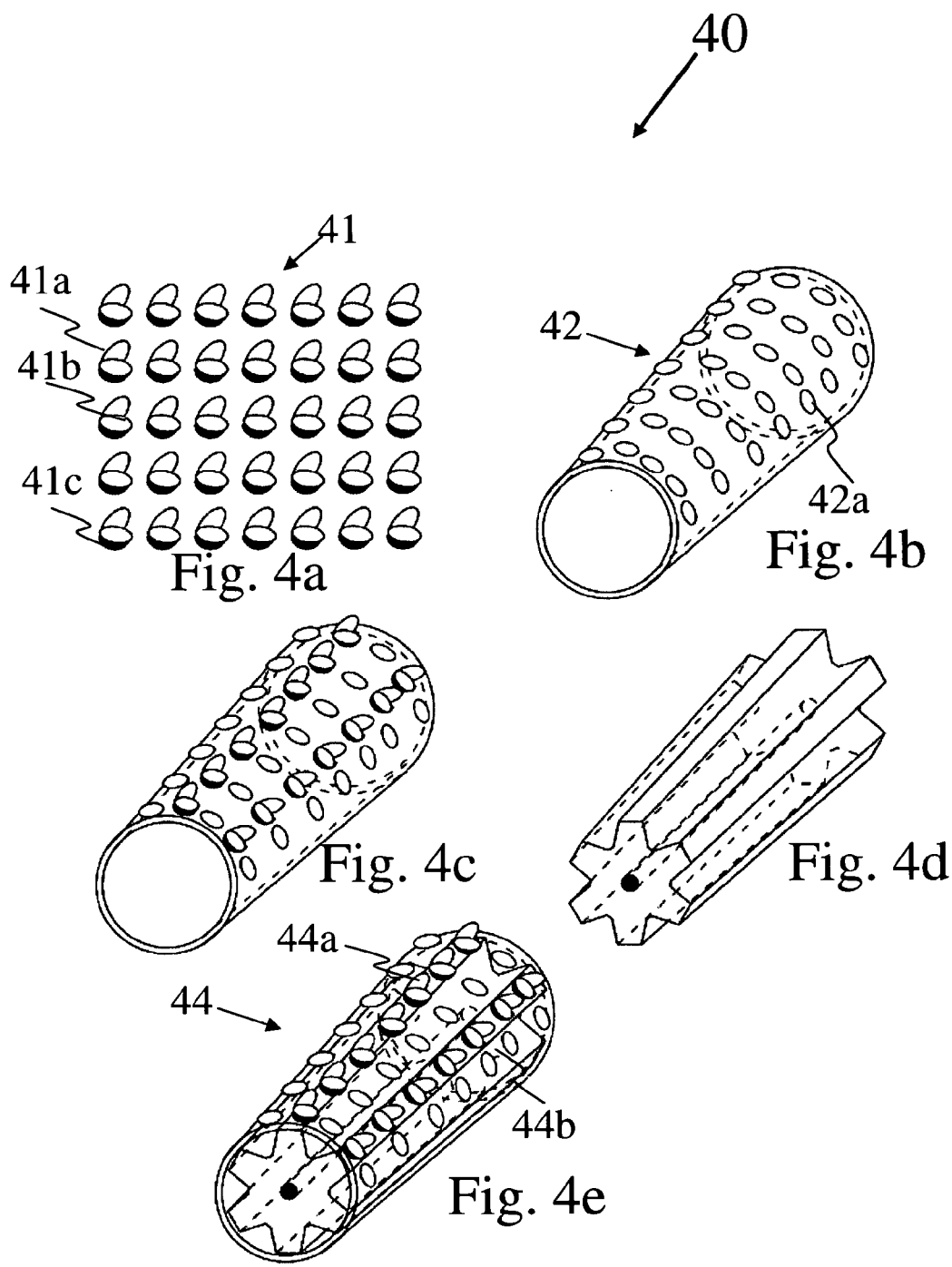
FIG. 4 depicts in five views FIG. 4a, FIG. 4b.

FIG. 4 depicts at 40 the mechanical details of the low cost modular disposable tapered hollow reamer according to the second embodiment of the invention in five views FIG. 4a, FIG. 4b, FIG. 4c, FIG. 4d and FIG. 4e. This mechanical design is similar to that disclosed in FIG. 3, but uses a polymeric sleeve with inserted cutting elements prior to pouring or injection molding of the polymeric portion instead of using metallic cutting sleeve. FIG. 4a illustrates a plurality of manufactured cutting elements 41 that have cutting protrusions 41a, characterized by the presence of an upward pointing cutting protrusion and a downward pointing anchoring protrusion attached to a ring member 41c. FIG. 4b schematically illustrates a conical hollow polymeric sleeve 42 with a plurality of apertures 42a. FIG. 4c illustrates insertion of cutting elements inserted into apertures along a line as shown, with the cutting elements 41a protruding along the outer surface of the polymeric sleeve, while the downward pointing anchoring protrusions of the cutting elements point inward towards the hollow center of the polymeric sleeve as shown. FIG. 4d shows the general shape of the poured or injection molded polymeric portion that fills in the hollow portion of the polymeric sleeve. FIG. 4e shows the manufactured low cost disposable tapered hollow reamer according to the second embodiment of the invention. The ridges 44a of the poured or injection molded polymeric portion contact the anchoring protrusions of the inserted cutting elements 41, while the portions of the poured or injection molded polymer portion are excluded in areas 44b forming a channel that serves as a space for collecting bone fragments or bone cement debris. Note that this channel is directly below the apertures in the polymeric sleeve. The polymeric sleeve and the poured or injection molded polymer is a medically compatible resin such as an acetyl resin or a polysulfone resin. The polymeric portion has a central aperture 33a drilled to receive a reusable shaft. On the opposite side, (not shown) the polymeric portion has two or more slots machined to engage with the torque transmitting tabs (21c of FIG. 2) of the shaft.

Figure 5:
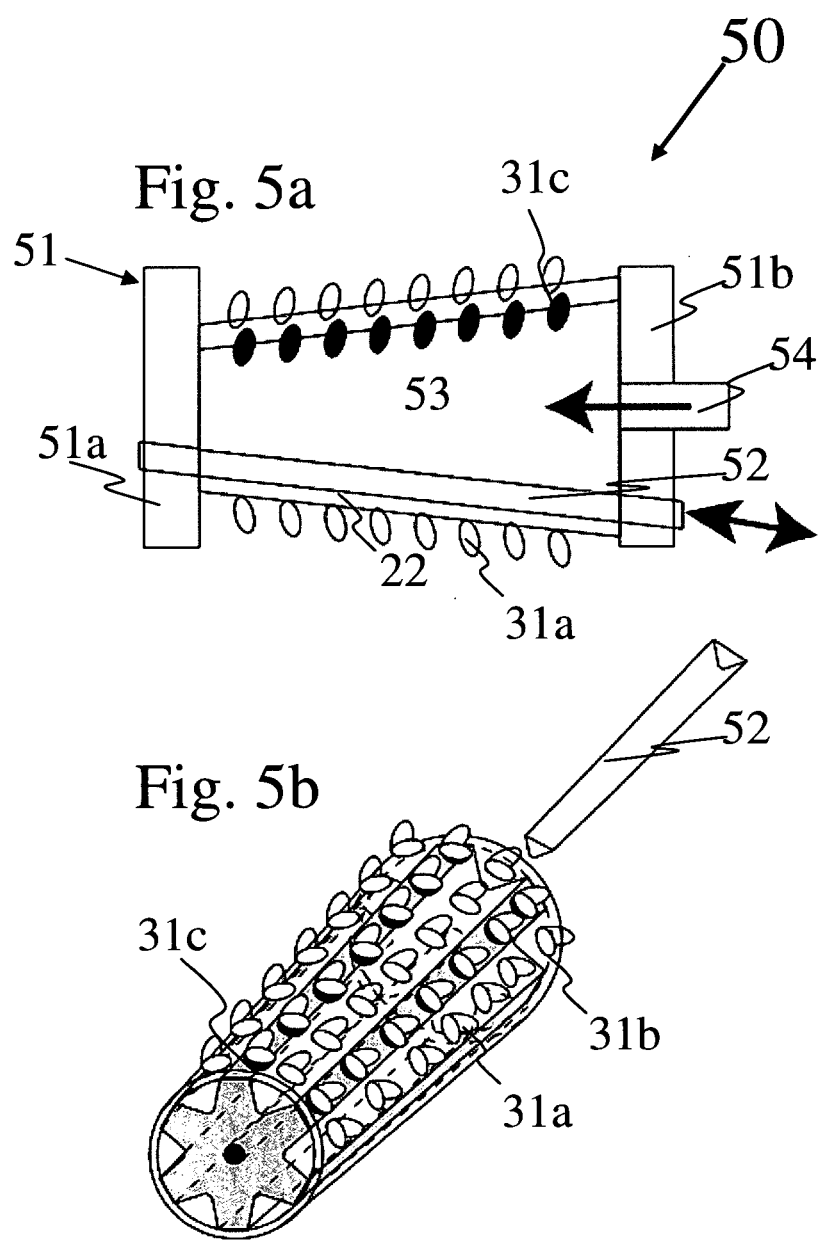
FIG. 5 depicts in two views, FIG. 5a and FIG. 5b, the manufacturing process for the low cost disposable hollow tapered reamer.

FIG. 5 illustrates at 50 the manufacturing process for the low cost disposable hollow reamer of the present invention in two views FIG. 5a and FIG. 5b. FIG. 5a illustrates at 51 an injection molding machine or a polymer pouring machine. The machine has two plates 51a and 51b clamping tightly a metallic cutter sleeve 22. The sleeve has a plurality of cutting teeth 31a protruding outward from its external surface, apertures 31b and attachment protrusions 31c pointing into the hollow portion of the sleeve. The polymer in this portion forms a ridge connecting the polymer portion with the metallic cutter sleeve at the anchoring attachment protrusions. Several removable bars 52 (only one shown for simplicity) is inserted at locations where only apertures 31b are present to create a space for colleting bone fragments or bone cement debris and is removed along the direction of the arrows shown. The polymer 53 enters through the port 54 filling the mold to form the low cost disposable hollow tapered reamer. FIG. 5b which depicts the manufactured low cost disposable hollow tapered reamer according to the first embodiment of the invention and the bar 52 is withdrawn before removing the manufactured part from the mold. The method of manufacture according to the second embodiment is exactly similar except that the polymeric sleeve is first fitted with cutting elements and inserted into the mold in exactly in the same manner and the removable bars positioned at the apertures where no cutting elements are present.

Multiple disposable tapered hollow sleeves can be attached to a single shaft. Preferably, a single shaft will attach to at least three different sized low cost disposable hollow cutters. This provides for the ability to combine various sized shafts with various sized disposable hollow cutter assemblies. These reusable reamer shafts have a coupling on the proximal end and a threaded portion in the distal end. Each reusable shaft has two or more torque transmitting tabs for receiving the slots of the low cost disposable tapered hollow reamer, as shown in FIG. 2, and a threaded portion at the distal end for retaining the modular pilot in accordance with the invention.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A modular tapered hollow reamer for medical applications, comprising:

a. a shaft portion having an elongated body with a proximal end, a central portion, and a distal end, said proximal end having a coupling portion appointed for attachment of said reamer to a drilling device, said central portion having two or more torque transmitting tabs integrally attached thereto, and said distal end having a male threaded portion;

b. a disposable tapered hollow reamer portion, comprising:
    1. a tapered hollow reamer sleeve having a plurality of externally protruding cutters, a plurality of apertures extending through a thickness of the sleeve and inwardly protruding anchoring projections;
    2. a central molded polymeric portion contacting said reamer sleeve at cutting teeth anchoring locations;
    3. said central molded polymeric portion having molded channels directly below apertures forming a space for collection of bone fragments or bone cement debris;
    4. said central molded polymeric portion having a central aperture for receiving said shaft and having two or more slots extending from said central aperture to receive said torque transmitting tabs;

c. two end plates one at each end of the proximal and distal ends containing said disposable tapered hollow reamer at each end to contain bone fragment or bone debris within a collection space;

d. a modular pilot with a central aperture having female threading;

e. said disposable tapered hollow reamer being adapted to slide over said distal end of said shaft portion causing said torque transmitting tabs of said shaft to engage with slots of said tapered hollow reamer sleeve;

f. said shaft portion being adapted to span the length of said disposable tapered Hollow reamer's interior;

g. said modular pilot being inserted at the distal end of said shaft portion engaging said male threaded portion, thereby attaching to said disposable tapered hollow reamer portion; and h. said distal end of said shaft portion being closed;

whereby, during drilling, torque from the shaft portion is transferred to said disposable tapered hollow reamer portion with substantial coincidence of centerlines, preventing reamer wobbliness, and bone and bone cement debris are collected in the space within the central molded polymeric portion.

2. A reamer for medical applications as recited by claim 1, wherein said central molded polymeric is formed of a medically compatible polymer comprising acetyl polymer and polysulfone polymer.

3. A reamer for medical applications as recited by claim 2, wherein said central molded polymeric portion is injection molded.

4. A reamer for medical applications as recited by claim 2, wherein said central molded polymeric portion is hot poured into the mold.

5. A reamer for medical applications as recited by claim 1, wherein said tapered hollow reamer sleeve is a metallic cutter sleeve.

6. A reamer for medical applications as recited by claim 5, wherein said metallic cutter sleeve has externally protruding cutters at the same location as said inwardly protruding anchoring projections.

7. A reamer for medical applications as recited by claim 5, wherein said metallic cutter sleeve has externally protruding cutters at the same location for each of said protruding cutters as said inwardly protruding anchoring projections.

8. A reamer for medical applications as recited by claim 1, wherein said tapered hollow reamer sleeve is a polymeric sleeve with inserted cutter elements.

9. A reamer for medical applications as recited by claim 8, wherein said cutter elements each have a cutting extension, ring portion and anchoring extension present at the same location.

10. A reamer for medical applications as recited by claim 1, wherein said elongated body of said shaft portion further comprises a marking to indicate its size.

11. A reamer for medical applications as recited by claim 1, wherein said modular pilot further comprises a marking to indicate its size.

12. A reamer for medical applications as recited by claim 1, wherein said disposable hollow reamer portion is appointed for a single, one-time use.

13. A reamer for medical applications as recited by claim 1, wherein said shaft portion is rigid.

14. A reamer for medical applications as recited by claim 1, wherein said shaft portion is flexible.

* * * * *